(12) United States Patent
Liu et al.

(10) Patent No.: US 11,845,710 B2
(45) Date of Patent: Dec. 19, 2023

(54) METHOD FOR CONTINUOUSLY PREPARING CITALOPRAM DIOL

(71) Applicants: ZHEJIANG HUAHAI PHARMACEUTICAL CO., LTD, Zhejiang (CN); SHANGHAI AOBO PHARMTECH, INC., LTD., Shanghai (CN)

(72) Inventors: Chen Liu, Shanghai (CN); Xing Li, Shanghai (CN); Huaxiang Ye, Shanghai (CN); Jicheng Zhang, Shanghai (CN); Luning Huang, Shanghai (CN); Anping Tao, Shanghai (CN); Jianguo An, Shanghai (CN); Hong Gu, Shanghai (CN)

(73) Assignees: ZHEJIANG HUAHAI PHARMACEUTICAL CO., LTD, Zhejiang (CN); SHANGHAI AOBO PHARMTECH, INC., LTD., Shanghai (CN)

( * ) Notice: Subject to any disclaimer, the term of this patent is extended or adjusted under 35 U.S.C. 154(b) by 379 days.

(21) Appl. No.: 17/312,635

(22) PCT Filed: Dec. 2, 2019

(86) PCT No.: PCT/CN2019/122455
§ 371 (c)(1),
(2) Date: Jun. 10, 2021

(87) PCT Pub. No.: WO2020/119507
PCT Pub. Date: Jun. 18, 2020

(65) Prior Publication Data
US 2022/0024860 A1 Jan. 27, 2022

(30) Foreign Application Priority Data

Dec. 12, 2018 (CN) .......................... 201811518150.6

(51) Int. Cl.
*C07C 253/30* (2006.01)
(52) U.S. Cl.
CPC .................. *C07C 253/30* (2013.01)

(58) Field of Classification Search
CPC ..................................................... C07C 253/30
USPC ........................................................... 558/422
See application file for complete search history.

(56) References Cited

U.S. PATENT DOCUMENTS

2008/0119662 A1    5/2008  Babu et al.

FOREIGN PATENT DOCUMENTS

| CN | 1875013 A | 12/2006 |
|---|---|---|
| CN | 102675152 A | 9/2012 |
| CN | 103896737 A | 7/2014 |
| CN | 105294496 A | 2/2016 |
| CN | 105348045 A | 2/2016 |
| CN | 106892837 A | 6/2017 |
| CN | 107848958 A | 3/2018 |
| WO | 2005077927 A1 | 8/2005 |
| WO | 2010004575 A2 | 1/2010 |

OTHER PUBLICATIONS

Office Action in corresponding/related Chinese Application No. 201811518150.6 dated Jan. 12, 2023.
International Search Report / Written Opinion dated Mar. 2, 2020 in related/corresponding PCT Application No. PCT/CN2019/122455, including partial English language translation.

*Primary Examiner* — Kristin A Vajda
(74) *Attorney, Agent, or Firm* — PATENT PORTFOLIO BUILDERS PLLC

(57) ABSTRACT

The present application relates to a method for citalopram intermediate citalopram diol. The method comprises: first mixing two Grignard reagents required for a reaction; then mixing the mixed Grignard reagents with a raw material 5-cyanophthalide in a temperature-controllable micromixer to obtain a reaction solution; then subjecting the reaction solution to the reaction by means of a reactor to obtain a citalopram diol reaction solution; and then performing operations such as quenching, concentration, extraction, acidification, and crystallization to obtain a qualified product. The citalopram diol provided in the present invention has good selectivity, high yield, high safety, safety and reliability, and little sewage discharge, and is suitable for industrial production.

20 Claims, No Drawings

METHOD FOR CONTINUOUSLY PREPARING CITALOPRAM DIOL

The present application claims the priority of the Chinese Patent Application NO. 201811518150.6, with the title of "METHOD FOR CONTINUOUSLY PREPARING CITALOPRAM DIOL", filed on Dec. 12, 2018 before the China National Intellectual Property Administration, which is hereby incorporated by reference in its entirety.

FIELD OF THE INVENTION

The present application relates to pharmaceutical and chemical industry, in particular to a method for continuously preparing citalopram diol.

BACKGROUND OF THE INVENTION

Citalopram and its isomer (S(+) citalopram) are selective serotonin reuptake inhibitors (SSRIs), which are clinically used for treating anxiety and depression. citalopram diol, citalopram diol hydrochloride or citalopram diol hydrobromide are important intermediates for preparing citalopram. Citalopram diol, whose chemical name is 4-(4-dimethylamino-1-(4-fluorophenyl)-1-hydroxybutyl)-3-(hydroxymethyl)benzonitrile, CAS number of 103146-25-4, has a structural formula as shown in formula 1:

formula 1

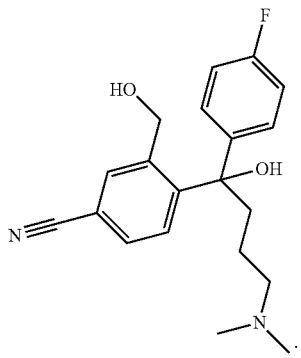

In general, citalopram diol is prepared by the reaction of 5-cyanophthalide (formula 2) with 4-fluorophenyl magnesium halide (formula 3) and 3-(N,N-dimethylamino) propylmagnesium halide (formula 4). More specifically, Grignard reagent of formula 3 is added to 5-cyanophthalide of formula 2 dropwise, and then Grignard reagent of formula 4 is added dropwise after holding for a certain period of time to prepare citalopram diol of formula 1. The process route is as follows:

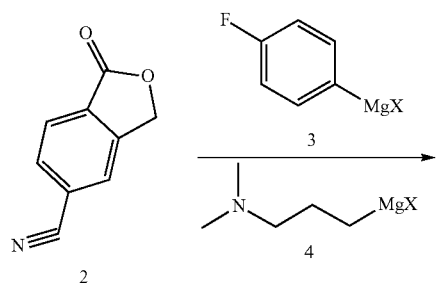

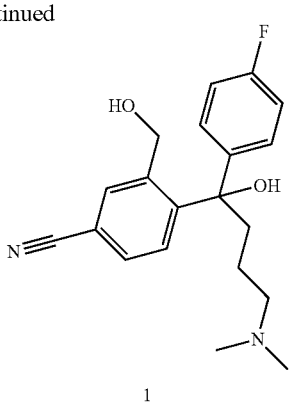

wherein, X=Cl, Br, I.

This process route can produce many impurities, e.g. bimolecular impurities produced by the bimolecular reaction of Grignard reagents themselves and the reaction of bimolecular Grignard reagents with substrates, etc. The major impurities produced are shown in Table 1:

TABLE 1

Major impurities during the process for preparing citalopram diol

| Name of impurities | Structure | Description |
|---|---|---|
| Impurity 1 | 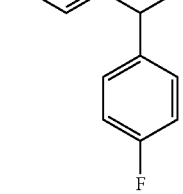 | Intermediate from the reaction of Grignard reagent of formula 3 with the raw material of formula 2 |
| Impurity 2 | 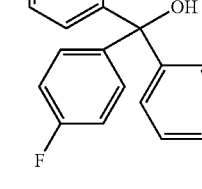 | Impurity from the reaction of bimolecular Grignard reagent of formula 3 with the raw material of formula 2 |
| Impurity 3 | 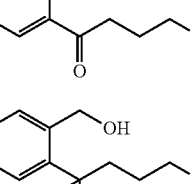 | Impurity from the reaction of Grignard reagent of formula 4 with the raw material of formula 2 |
| Impurity 4 | 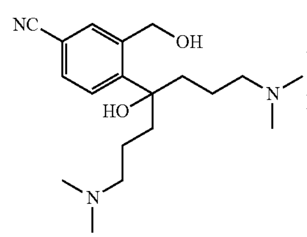 | Impurity from the reaction of bimolecular Grignard reagent of formula 4 with the raw material of formula 2 |

The major impurities above have direct influence on the yield of citalopram diol: the more impurities produced, the lower the yield of citalopram diol. The reaction itself is not difficult to carry out, but a key challenge is how to improve the selectivity of the reaction to reduce the generation of impurities, thereby improving the yield. Therefore, the most important thing for improving the yield of citalopram diol is to control the generation of the major impurities listed in Table 1.

One-pot process is used to prepare citalopram diol in patent document WO2005077927A1, which comprises: reacting 5-cyanophthalide of formula 2 with Grignard reagent of formula 3; after the reaction is completed, adding 3.0 e.q. Grignard reagent of formula 4 at 0-5° C.; and post-processing after the reaction is completed. In this method, it is necessary to add two Grignard reagents dropwise to the reaction system separately, the operation is troublesome and it takes a long time. Besides, the key challenge of reaction selectivity is not mentioned, and the generation of impurities is not discussed.

Patent document WO2010004575A2 discloses that 5-cyanophthalide of formula 2 is reacted with Grignard reagent of formula 3 and Grignard reagent of formula 4 to synthesize citalopram diol. In this patent, the amounts of Grignard reagent of formula 3 and Grignard reagent of formula 4 are reduced to 1.2-1.5 e.q., and more types of reactive solvents can be used, e.g. tetrahydrofuran, 2-methyltetrahydrofuran, diethyl ether, isopropyl ether, methyl tert-butyl ether, petroleum ether, etc. The method of this patent also comprises adding Grignard reagents into the reaction system in sequence, and the reaction selectivity of Grignard reagents is not mentioned, either. In the example C of this patent, 50 g of 5-cyanophthalide of formula 2 is used to prepare 70 g of crude citalopram diol. The yield of the crude product is calculated to be 65.18%, which is low and the preparation result is not ideal.

Patent document CN105294496A discloses that 2-methyltetrahydrofuran can be used as a reaction solvent to obtain citalopram diol with high purity and high yield, which mainly comprises the following two steps: in the first step, 5-cyanophthalide of formula 2 is reacted with Grignard reagent of formula 3, then intermediates are obtained by post-processing; and in the second step, the intermediates obtained in the first step are reacted with Grignard reagent of formula 4 to obtain citalopram diol. In this reaction, the content of impurity 2 generated in the first step is still high (8.66%); when monitored by HPLC, the content of the intermediates obtained in the first step is 87.55%, and the content of the citalopram diol obtained in the second step is up to 89.35%. The yield of this patent by using 2-methyltetrahydrofuran is 76.9%, which is not high. The yield of the method in this patent is not ideal, because the method not only needs to add Grignard reagents dropwise in batches, but also to carry out post-processing twice. One pot process is not used in this method to synthesize citalopram diol, the operation is more complex, the operation period is long, the preparation cost is high and this method has no advantage when applying to industrial production.

Currently the primary method for preparing citalopram diol comprises adding Grignard reagent of formula 3 dropwise to react with 5-cyanophthalide of formula 2, and then adding Grignard reagent of formula 4 dropwise for the reaction. The operation of this method is troublesome and the generation of major impurities (in particular impurity 2) cannot be controlled well. Further, since the Grignard reagent is added into the reaction system dropwise, the production period is long, and the use of the Grignard reagent has a certain safety risk. There is a need to develop a method for continuously preparing citalopram diol to solve these problems.

SUMMARY OF THE INVENTION

The present application provides a method for continuously preparing citalopram diol, which is simple in operation, safety and feasibility. The method has less by-products, high yield and high efficiency, and is suitable for industrial production.

The technical solution is as follows:

A method for continuously preparing citalopram diol, comprising:
(1) preparing an organic solvent feed liquid A containing 5-cyanophthalide of formula 2;
(2) preparing a mixed feed liquid B containing Grignard reagent of formula 3 and Grignard reagent of formula 4;
(3) mixing the organic solvent feed liquid A in step (1) with the mixed feed liquid B in step (2) by a temperature-controllable micromixer to obtain a reaction solution C;
(4) reacting the reaction solution C in a reactor to obtain a reaction solution containing citalopram diol of formula 1; and
(5) post-processing the reaction solution containing citalopram diol obtained in step (4) to obtain a citalopram diol salt; preferably, the citalopram diol salt is at least one of hydrochloride, hydrobromide, sulfate or phosphate;

The reaction scheme is as follows:

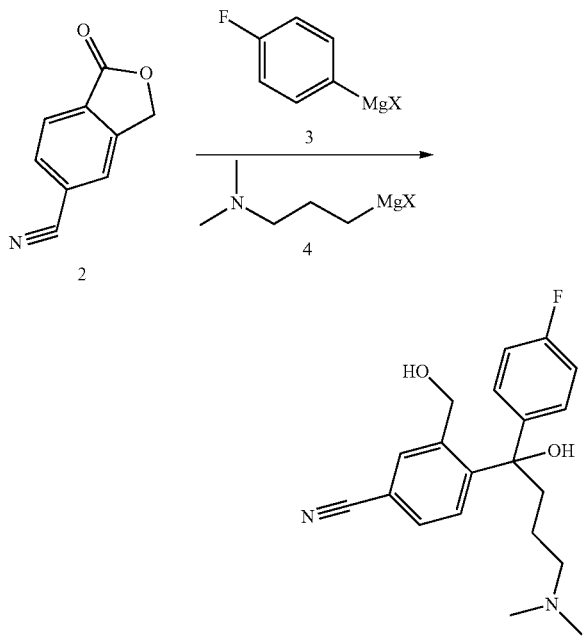

wherein, X is Cl, Br or I.

The present application provides a pioneering method, which comprises mixing Grignard reagent of formula 3 with Grignard reagent of formula 4 at first, and then continuously reacting with 5-cyanophthalide of formula 2 to prepare citalopram diol of formula 1. In the specific process, the mixed feed liquid B containing Grignard reagent of formula 3 and Grignard reagent of formula 4, and the organic solvent feed liquid A of 5-cyanophthalide can pass through a material conveying equipment (e.g. feed pump, gravity-flow meter, one-way valve, etc.) and can be mixed continuously by the temperature-controllable micromixer. The resulting reaction solution C can continuously flow into the reactor to obtain the reaction solution containing citalopram diol. The reaction solution obtained by the method of the present application has high selectivity and low impurity, which can be post-processed to obtain citalopram diol salt with a high yield and high purity.

In step (1), the organic solvent feed liquid A can be prepared by stirring 5-cyanophthalide in the organic solvent; in some embodiments of the present application, the organic solvent of the organic solvent feed liquid A can be at least one organic solvent selected from the group consisting of diethyl ether, tetrahydrofuran, 2-methyltetrahydrofuran, 1,4-dioxane, toluene, anisole, cyclohexane, n-hexane, xylene, 1,2-dimethoxyethane, ethylene glycol diethyl ether and diphenyl ether, preferably at least one of diethyl ether, tetrahydrofuran, 2-methyltetrahydrofuran or toluene. In other embodiments of the present application, 5-cyanophthalide in the organic solvent feed liquid A has a molar concentration of 0.001 to 5.0 mmol/g, preferably 0.01 to 3.0 mmol/g, more preferably 0.1 to 2.0 mmol/g.

In step (2), Grignard reagent of formula 3 and Grignard reagent of formula 4 can be prepared by the methods well known to those skilled in the art. Specifically, Grignard reagent of formula 3 used in the present application can be prepared by adding magnesium to its corresponding halide in an organic solvent or adding magnesium and catalytic amount of iodine to its corresponding halide in an organic followed by heating; Grignard reagent of formula 4 can be prepared by adding magnesium to its corresponding halide in an organic solvent or adding magnesium and catalytic amount of iodine to its corresponding halide in an organic solvent followed by heating. During the preparation process, the reaction temperature is 20 to 100° C. Specifically, the organic solvent for preparing Grignard reagent can be at least one organic solvent selected from the group consisting of diethyl ether, tetrahydrofuran, 2-methyltetrahydrofuran, 1,4-dioxane, anisole, 1,2-dimethoxyethane, ethylene glycol diethyl ether or diphenyl ether. More preferably, the organic solvent can be at least one organic solvent selected from the group consisting of diethyl ether, tetrahydrofuran and 2-methyltetrahydrofuran.

Grignard reagents prepared by the previous method is filtered, and then Grignard reagent of formula 3 is mixed with Grignard reagent of formula 4 in a certain ratio to obtain the mixed feed liquid B. In some embodiments of the present application, a molar ratio of Grignard reagent of formula 3 and Grignard reagent of formula 4 is 0.7~1.5:1.0, preferably 1.0:1.0. In other embodiments of the present application, molar concentrations of Grignard reagent of formula 3 and Grignard reagent of formula 4 are 0.001 to 5.0 mmol/g, respectively, preferably 0.01 to 3.0 mmol/g, more preferably 0.1 to 2.0 mmol/g.

In some embodiments of the present application, the organic solvent of the organic solvent feed liquid B is at least one organic solvent selected from the group consisting of diethyl ether, tetrahydrofuran, 2-methyltetrahydrofuran, 1,4-dioxane, toluene, anisole, cyclohexane, n-hexane, xylene, 1,2-dimethoxyethane, ethylene glycol diethyl ether and diphenyl ether, preferably at least one of diethyl ether, tetrahydrofuran, 2-methyltetrahydrofuran or toluene.

In some embodiments of the present application, a flow ratio of feed liquid A and feed liquid B passing through the micromixer in step (3) is 1.0:0.1~10.0 and a passing temperature is −30~80° C., preferably −10~30° C.

In the present application, "passing temperature" can be understood as the temperature of the micromixer.

In the present application, the flow passing through the micromixer can be understood as the flow entering into the micromixer. The flow herein is mass flow.

In some embodiments of the present application, in the organic solvent feed liquid A and mixed feed liquid B in step (3), an initial molar ratio of Grignard reagent of formula 3 to the raw material 5-cyanophthalide is 1.0~2.0:1.0; an initial molar ratio of Grignard reagent of formula 4 to the raw material 5-cyanophthalide is 1.0~2.0:1.0.

In the present application, the initial molar ratio can be understood as the molar ratio of Grignard reagent and 5-cyanophthalide when entering into the micromixer.

In some embodiments of the present application, the temperature-controllable micromixer used in step (3) can be a temperature-controllable passive micromixer or a temperature-controllable active micromixer; preferably, the temperature-controllable passive micromixer is a stratified flow micromixer or a chaotic advection micromixer; the temperature-controllable active micromixer is selected from the group consisting of an ultrasonically actuated micromixer, an acoustic bubbling micromixer, a droplet micromixer, a magnetic micromixer and an electrokinetic micromixer.

In some embodiments of the present application, in step (3), a mixing temperature of the organic solvent feed liquid A and the mixed feed liquid B in step (2) in micromixer is −30 to 80° C., and a mixing time is 0.05 to 1 s.

In some embodiments of the present application, the reactor in step (4) is at least one reactor selected from the group consisting of a microchannel reactor, a static mixer and a tubular reactor.

In some embodiments of the present application, in step (4), a reaction temperature of the reaction solution C in the reactor is −30 to 80° C., preferably −20 to 50° C., more preferably −10 to 30° C.

In some embodiments of the present application, in step (4), a reaction time of the reaction solution C in the reactor is 0.01 to 10 min, preferably 0.1 to 3 min, more preferably 0.9 to 3 min.

In some embodiments of the present application, the post-processing in step (5) comprises: quenching the reaction solution, extracting, acidizing and extracting, crystallizing, and finally centrifugal drying to obtain the citalopram diol salt; optionally, concentrating after quenching.

More specifically, post-processing in step (5) is as follows:

quenching the reaction solution containing citalopram diol of formula 1 using at least one of saturated ammonium chloride solution, citric acid solution or water, to obtain a quenched reaction solution;

optionally, concentrating the quenched reaction solution, to obtain a concentrated reaction solution;

adding an extraction solvent to the quenched reaction solution or the concentrated reaction solution, removing a first aqueous phase after layering and retaining a first organic phase; the extraction solvent is an organic solvent insoluble with water, preferably ethyl acetate, toluene, diethyl ether or 2-methyltetrahydrofuran;

adding an acid aqueous solution to the first organic phase, removing a second organic phase after layering and retaining a second aqueous phase;

a pH of the second aqueous phase is 3.5-4.5; preferably, the acid is at least one acid selected from the group consisting of hydrochloric acid, hydrobromic acid, sulfuric acid and phosphoric acid;

cooling the second aqueous phase for crystallization, preferably adding inorganic salt, more preferably adding sodium chloride to assist crystallization; and centrifuging and drying a precipitated crystal to obtain the citalopram diol salt.

In the specific post-processing process, concentration can be atmospheric concentration or vacuum concentration, which can recycle the solvent to reduce the cost. If the organic solvents of organic solvent feed liquid A and mixed feed liquid B are water insoluble solvents, then the concentration may not be carried out, and an extraction solvent, e.g. toluene, can be added to the quenched reaction directly.

In the crystallization operation, inorganic salts are added to assist crystallization, so that the yield is improved.

The present application provides a pioneering method, which comprises mixing two Grignard reagents participating in the reaction in a certain ratio at first, and then continuously reacting with 5-cyanophthalide to prepare citalopram diol, achieving following beneficial effects.

Firstly, due to the continuous preparation of citalopram diol, the reaction selectivity is obviously improved, the generation of the impurity is controlled, and the reaction yield is improved.

Secondly, due to the continuous preparation of Grignard reaction of citalopram diol, the risk of the reaction is greatly decreased.

Thirdly, due to the continuous preparation of Grignard reaction of citalopram diol, the production process is simpler, the use of raw materials can be controlled more precisely, the cost is reduced, the emission of pollutants is reduced and the economic efficiency is improved.

Fourthly, during the reaction solution passing through the micromixer, the organic solvent feed liquid A and the mixed feed liquid B can be mixed well immediately thus reaching a stable reaction environment and easily realizing industrial scaling-up.

DETAILED DESCRIPTION OF THE INVENTION

In order to make the technical problems solved by the present application, technical solutions and technical effects more clear, the present application is described in detail by the following specific examples. In the following examples, unless otherwise stated, the specific conditions of the test method are generally implemented according to the conventional conditions or the conditions recommended by the manufacturer; the raw materials and reagents are obtained commercially or prepared using public information.

Example 1

(1) The preparation of the organic solvent feed liquid A: tetrahydrofuran solution of 5-cyanophthalide, with a concentration of 0.23 mmol/g.

The preparation of the mixed feed liquid B: tetrahydrofuran solutions of Grignard regents, 4-fluorophenylmagnesium bromide with a concentration of 0.19 mmol/g and 3,3-dimethylaminopropylmagnesium chloride with a concentration of 0.20 mmol/g.

(2) The feed liquid A and the feed liquid B in step (1) were continuously conveyed into the temperature-controllable stratified flow micromixer at 12.0 g/min and 15 g/min respectively for mixing; the mixing temperature was 25° C. and the mixing time was 0.1 s; the mixed reaction solution was continuously flowed into a microchannel reactor and reacted; the temperature of microchannel reactor was controlled at 10° C., and the dwell time was 2.6 min; the sample was taken at the outlet of reactor end and quenched by using saturated ammonium chloride solution, then the sample was tested to obtain a HPLC testing results of the reaction solution. The results were shown in Table 2.

(3) The reaction solution in step (2) was quenched with saturated ammonium chloride solution under 25-45° C. and concentrated to recycle the reaction solvent of tetrahydrofuran, toluene was added to extract, hydrochloric acid was added to adjust pH to 3.5-4.5, the aqueous phase was separated, sodium chloride was added to assist crystallization and finally the precipitated crystal was centrifuged and dried to obtain citalopram diol hydrochloride with a yield of 89.38%.

Example 2

(1) The preparation of the organic solvent feed liquid A: 2-methyltetrahydrofuran solution of 5-cyanophthalide with a concentration of 0.50 mmol/g.

The preparation of the mixed feed liquid B: diethyl ether solutions of Grignard regents, 4-fluorophenylmagnesium bromide with a concentration of 0.33 mmol/g and 3,3-dimethylaminopropylmagnesium chloride with a concentration of 0.33 mmol/g.

(2) The feed liquid A and the feed liquid B in step (1) were continuously conveyed into the temperature-controllable droplet micromixer at 15.0 g/min and 23 g/min respectively for mixing; the mixing temperature was 30° C. and the mixing time was 0.3 s; the mixed reaction solution was continuously flowed into a microchannel reactor and reacted; the temperature of microchannel reactor was controlled at 3° C., and the dwell time was 3.2 min; the sample was taken at the outlet of reactor end and quenched by using saturated ammonium chloride solution, then the sample was tested to obtain a HPLC testing results of the reaction solution. The results were shown in Table 2.

(3) The reaction solution in step (2) was quenched with saturated ammonium chloride solution under 25-45° C. and concentrated to recycle the reaction solvent of 2-methyltetrahydrofuran, toluene was added to extract, hydrochloric acid was added to adjust pH to 3.5-4.5, the aqueous phase was separated, sodium chloride was added to assist crystallization and finally the precipitated crystal was centrifuged and dried to obtain citalopram diol hydrochloride with a yield of 88.74%.

Example 3

(1) The preparation of the organic solvent feed liquid A: toluene solution of 5-cyanophthalide with a concentration of 0.30 mmol/g.

The preparation of the mixed feed liquid B: 2-methyltetrahydrofuran solutions of Grignard regents, 4-fluorophenylmagnesium bromide with a concentration of 0.36 mmol/g and 3,3-dimethylaminopropylmagnesium chloride with a concentration of 0.26 mmol/g.

(2) The feed liquid A and the feed liquid B in step (1) were continuously conveyed into the temperature-controllable stratified flow micromixer at 8.0 g/min and 12.6 g/min respectively for mixing; the mixing temperature was 35° C. and the mixing time was 0.3 s; the mixed reaction solution was continuously flowed into a microchannel reactor and reacted; the temperature of microchannel reactor was controlled at 80° C., and the dwell time was 0.9 min; the sample was taken at the outlet of reactor end and quenched by using saturated ammonium chloride solution, then the sample was tested to obtain a HPLC testing results of the reaction solution. The results were shown in Table 2.
(3) The reaction solution in step (2) was quenched with saturated ammonium chloride solution under 25-45° C. and concentrated to recycle the reaction solvent of 2-methyltetrahydrofuran, toluene was added to extract, hydrochloric acid was added to adjust pH to 3.5-4.5, the aqueous phase was separated, sodium chloride was added to assist crystallization and finally the precipitated crystal was centrifuged and dried to obtain citalopram diol hydrochloride with a yield of 88.26%.

Example 4

(1) The preparation of the organic solvent feed liquid A: tetrahydrofuran solution of 5-cyanophthalide with a concentration of 1.2 mmol/g.
The preparation of the mixed feed liquid B: tetrahydrofuran solutions of Grignard regents, 4-fluorophenylmagnesium bromide with a concentration of 1.0 mmol/g and 3,3-dimethylaminopropylmagnesium chloride with a concentration of 1.0 mmol/g.
(2) The feed liquid A and the feed liquid B in step (1) were continuously conveyed into the temperature-controllable stratified flow micromixer at 6.0 g/min and 7.8 g/min respectively for mixing; the mixing temperature was 60° C. and the mixing time was 0.5 s; the mixed reaction solution was continuously flowed into a microchannel reactor and reacted; the temperature of microchannel reactor was controlled at 10° C., and the dwell time was 9 min; the sample was taken at the outlet of reactor end and quenched by using saturated ammonium chloride solution, then the sample was tested to obtain a HPLC testing results of the reaction solution. The results were shown in Table 2.
(3) The reaction solution in step (2) was quenched with saturated ammonium chloride solution under 25-45° C. and concentrated to recycle the reaction solvent of tetrahydrofuran, toluene was added to extract, hydrochloric acid was added to adjust pH to 3.5-4.5, the aqueous phase was separated, sodium chloride was added to assist crystallization and finally the precipitated crystal was centrifuged and dried to obtain citalopram diol hydrobromide with a yield of 90.03%.

Example 5

(1) The preparation of the organic solvent feed liquid A: 2-methyltetrahydrofuran solution of 5-cyanophthalide with a concentration of 0.3 mmol/g.
The preparation of the mixed feed liquid B: 2-methyltetrahydrofuran solutions of Grignard regents, 4-fluorophenylmagnesium bromide with a concentration of 1.1 mmol/g and 3,3-dimethylaminopropylmagnesium chloride with a concentration of 1.0 mmol/g.
(2) The feed liquid A and the feed liquid B in step (1) were continuously conveyed into the temperature-controllable stratified flow micromixer at 20.0 g/min and 6 g/min respectively for mixing: the mixing temperature was 30° C. and the mixing time was 0.08 s; the mixed reaction solution was continuously flowed into a microchannel reactor and reacted; the temperature of microchannel reactor was controlled at 10° C., and the dwell time was 4.2 min, the sample was taken at the outlet of reactor end and quenched by using saturated ammonium chloride solution, then the sample was tested to obtain a HPLC testing results of the reaction solution. The results were shown in Table 2.
(3) The reaction solution in step (2) was quenched with saturated ammonium chloride solution under 25-45° C. and concentrated to recycle the reaction solvent of 2-methyltetrahydrofuran, toluene was added to extract, hydrochloric acid was added to adjust pH to 3.5-4.5, the aqueous phase was separated, sodium chloride was added to assist crystallization and finally the precipitated crystal was centrifuged and dried to obtain citalopram diol hydrobromide with a yield of 89.55%.

Example 6

(1) The preparation of the organic solvent feed liquid A: tetrahydrofuran solution of 5-cyanophthalide with a concentration of 0.4 mmol/g.
The preparation of the mixed feed liquid B: tetrahydrofuran solutions of Grignard regents, 4-fluorophenylmagnesium bromide with a concentration of 1.3 mmol/g and 3,3-dimethylaminopropylmagnesium chloride with a concentration of 1.5 mmol/g.
(2) The feed liquid A and the feed liquid B in step (1) were continuously conveyed into the temperature-controllable stratified flow micromixer at 12.0 g/min and 5.9 g/min respectively for mixing; the mixing temperature was 30° C. and the mixing time was 0.2 s; the mixed reaction solution was continuously flowed into a microchannel reactor and reacted; the temperature of microchannel reactor was controlled at 10° C., and the dwell time was 4 min; the sample was quenched at the outlet of reactor end by using saturated ammonium chloride solution, then the sample was tested to obtain a HPLC testing results of the reaction solution. The results were shown in Table 2.
(3) The quenched reaction solution in step (2) was concentrated to recycle the reaction solvent of tetrahydrofuran, toluene was added to extract, hydrochloric acid was added to adjust pH to 3.5-4.5, the aqueous phase was separated, sodium chloride was added to assist crystallization and finally the precipitated crystal was centrifuged and dried to obtain citalopram diol hydrobromide with a yield of 89.16%.

Example 7

(1) The preparation of the organic solvent feed liquid A: tetrahydrofuran solution of 5-cyanophthalide with a concentration of 0.53 mmol/g.
The preparation of the mixed feed liquid B: tetrahydrofuran solutions of Grignard regents, 4-fluorophenylmagnesium bromide with a concentration of 0.88 mmol/g and 3,3-dimethylaminopropylmagnesium chloride with a concentration of 0.89 mmol/g.
(2) The feed liquid A and the feed liquid B in step (1) were continuously conveyed into the temperature-controllable stratified flow micromixer at 14.0 g/min and 9.3 g/min respectively for mixing; the mixing temperature was 50° C. and the mixing time was 0.1 s; the mixed reaction solution was continuously flowed into a microchannel reactor and reacted; the temperature of microchannel reactor was controlled at 10° C. The feed liquid A and the feed liquid B in step (1) were continuously conveyed into the microchannel reactor at 14.0 g/min and 9.3 g/min respectively, and the dwell time was 1.7 min; the sample was quenched at the outlet of reactor end by using saturated ammonium chloride solution, then the sample was tested to obtain a HPLC testing results of the reaction solution. The results were shown in Table 2.
The quenched reaction solution in step (2) was quenched with saturated ammonium chloride solution under 25-45° C. and concentrated to recycle the reaction solvent of tetrahydrofuran, toluene was added to extract, hydrochloric acid was added to adjust pH to 3.5-4.5, the aqueous phase was separated, sodium chloride was added to assist crystallization and finally the precipitated crystal was centrifuged dried to obtain citalopram diol hydrochloride with a yield of 91.17%.

TABLE 2

Test results of the continuous prepared citalopram diol of Examples 1-7

HPLC testing results of the reaction solution

| Example | Content of 5-cyanophthalide/% | Content of citalopram diol/% | Content of impurity 1/% | Content of impurity 2/% | Content of impurity 3/% | Content of impurity 4/% | Yield of citalopram diol salt/% |
|---|---|---|---|---|---|---|---|
| Example 1 | 0.1 | 87.73 | 0.68 | 3.64 | 0.24 | 0.31 | 89.38 |
| Example 2 | 0.1 | 86.69 | 0.39 | 3.98 | 0.29 | 0.25 | 88.74 |
| Example 3 | 0.3 | 88.16 | 0.62 | 2.90 | 0.67 | 0.19 | 88.26 |
| Example 4 | 0   | 89.24 | 0.59 | 2.42 | 0.35 | 0.28 | 90.03 |
| Example 5 | 0.1 | 87.93 | 0.47 | 2.98 | 0.26 | 0.34 | 89.55 |
| Example 6 | 0.2 | 87.56 | 0.61 | 3.13 | 0.22 | 0.27 | 89.16 |
| Example 7 | 0   | 90.29 | 0.44 | 2.16 | 0.18 | 0.16 | 91.17 |

Comparative Example 1

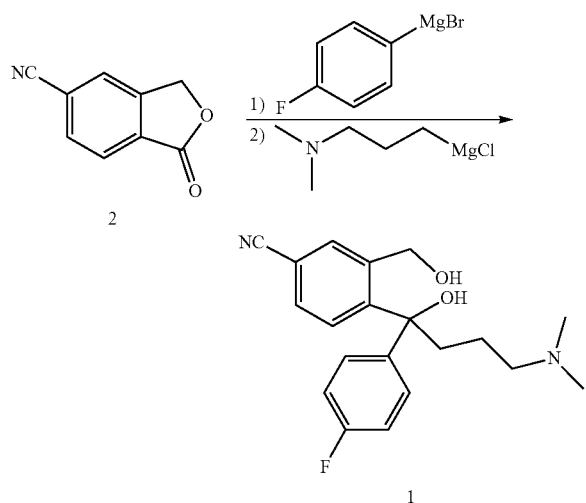

66 kg of 5-cyanophthalide of formula 2 and 420 L of tetrahydrofuran were added into a reactor, the temperature was reduced to 0-5° C. under the protection of nitrogen, and 200 kg of tetrahydrofuran solution of 0.00273 mmol/g 4-fluorophenylmagnesium bromide (the equivalent of 4-fluorophenylmagnesium bromide was 1.32) was added dropwise into the reactor at −5-5° C. It took 3.0 hours to complete the addition. The reactor was kept at 0-5° C. for 2 h, and 300 kg of tetrahydrofuran solution of 0.00164 mol/kg 3,3-dimethylaminopropylmagnesium chloride (the equivalent of 3,3-dimethylaminopropylmagnesium chloride was 1.19) was added dropwise into the reactor at 0-5° C. It took 4.5 hours to complete the addition. The reaction solution was quenched immediately, and a sample was taken for analysis. After concentration, extraction, acidification, crystallization, etc., the hydrochloride of formula 1 (110 kg) was obtained with a yield of 77.46%. The sample analysis results after quenching were as follows:

| Content of 5-cyanophthalide/% | Content of citalopram diol/% | Content of impurity 1/% | Content of impurity 2/% | Content of impurity 3/% | Content of impurity 4/% |
|---|---|---|---|---|---|
| 0.1 | 78.07 | 3.57 | 9.62 | 2.33 | 3.91 |

Comparative Example 2

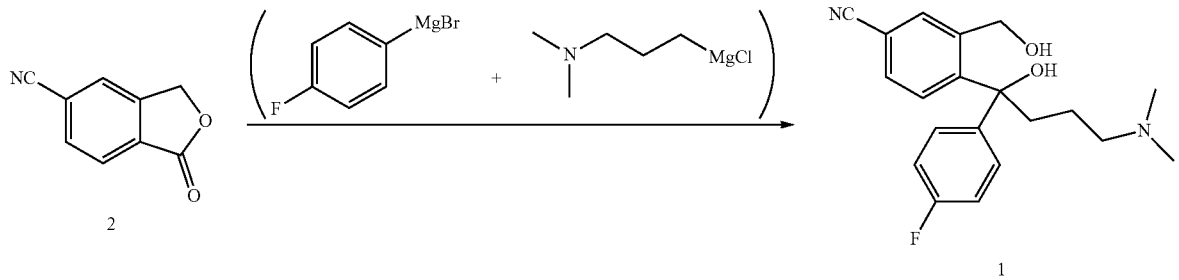

150 g of tetrahydrofuran solution of 0.0023 mol/g 4-fluorophenylmagnesium bromide (the equivalent of 4-fluorophenyl magnesium bromide was 1.10) and 160 g of tetrahydrofuran solution of 0.0021 mol/g 3,3-dimethylaminopropylmagnesium chloride (the equivalent of 3,3-dimethylaminopropylmagnesium chloride was 1.07) were added to a dropping vessel at 0-5° C. for subsequent use. 50.0 g of 5-cyanophthalide of formula 2 and 150 mL of tetrahydrofuran were added into the reactor, the temperature was reduced to −5-5° C. under the protection of nitrogen, and the mixed solution in the dropping vessel was added into the reactor dropwise at −5-5° C. It took 2 hours to complete the addition. The reaction solution was quenched after reacting for 2 h, then a sample was taken for analysis. After concentration, extraction, acidification, crystallization, etc., the hydrochloride of formula 1 (81.23 g) was obtained with a yield of 75.50%. The sample analysis results after quenching were as follows:

| Content of 5-cyanophthalide/% | Content of citalopram diol/% | Content of impurity 1/% | Content of impurity 2/% | Content of impurity 3/% | Content of impurity 4/% |
| --- | --- | --- | --- | --- | --- |
| 0.11 | 75.03 | 1.39 | 13.02 | 3.38 | 5.47 |

The above-mentioned examples are used to explain the substantive content of the present application, not to limit the protection scope of the present application. Those skilled in the art should understand that the technical solutions of the present application can be modified or equivalently replaced without departing from the substance and protection scope of the technical solutions of the present application.

The invention claimed is:

1. A method for continuously preparing citalopram diol or a citalopram diol salt, comprising:
   (1) preparing an organic solvent feed liquid A containing 5-cyanophthalide of formula 2;
   (2) preparing a mixed feed liquid B containing Grignard reagent of formula 3 and Grignard reagent of formula 4;
   (3) mixing the organic solvent feed liquid A in step (1) with the mixed feed liquid B in step (2) by a temperature-controllable micromixer to obtain a reaction solution C;
   (4) reacting the reaction solution C in a reactor to obtain a reaction solution containing citalopram diol of formula 1; and optionally
   (5) post-treating the reaction solution containing citalopram diol obtained in step (4) to obtain a citalopram diol salt;
   wherein, the reaction scheme is as follows:

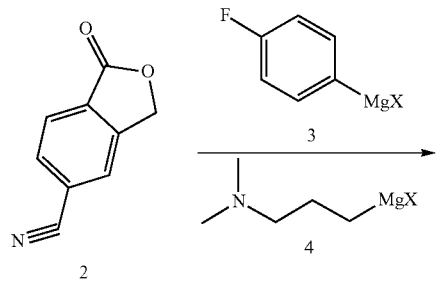

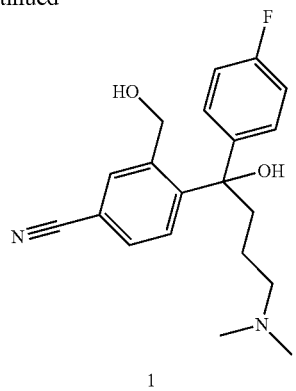

wherein, X is Cl, Br or I.

2. The method according to claim 1, wherein a molar concentration of 5-cyanophthalide in the organic solvent feed liquid A is 0.001-5.0 mmol/g.

3. The method according to claim 1, wherein the organic solvent of the organic solvent feed liquid A is at least one organic solvent selected from the group consisting of diethyl ether, tetrahydrofuran, 2-methyltetrahydrofuran, 1,4-dioxane, toluene, anisole, cyclohexane, n-hexane, xylene, 1,2-dimethoxyethane, ethylene glycol diethyl ether and diphenyl ether.

4. The method according to claim 1, wherein an organic solvent of the mixed feed liquid B is at least one organic solvent selected from the group consisting of diethyl ether, tetrahydrofuran, 2-methyltetrahydrofuran, 1,4-dioxane, toluene, anisole, cyclohexane, n-hexane, xylene, 1,2-dimethoxyethane, ethylene glycol diethyl ether and diphenyl ether.

5. The method according to claim 1, wherein a molar ratio of Grignard reagent of formula 3 to Grignard reagent of formula 4 in the mixed feed liquid B is 0.7-1.5:1.0.

6. The method according to claim 1, wherein molar concentrations of Grignard reagent of formula 3 and Grignard reagent of formula 4 in the mixed feed liquid B are 0.001 to 5.0 mmol/g, respectively.

7. The method according to claim 1, wherein a flow ratio of the organic solvent feed liquid A to the mixed feed liquid B passing through the micromixer in step (3) is 1.0:0.1-10.0, a passing temperature is −30 to 80° C., and a mixing time is 0.05 to 1 s.

8. The method according to claim 1, wherein in the organic solvent feed liquid A and the mixed feed liquid B in step (3), an initial molar ratio of Grignard reagent of formula 3 to 5-cyanophthalide is 1.0-2.0:1.0; and an initial molar ratio of Grignard reagent of formula 4 to 5-cyanophthalide is 1.0-2.0:1.0.

9. The method according to claim 1, wherein the temperature-controllable micromixer is a temperature-controllable passive micromixer or a temperature-controllable active micromixer.

10. The method according to claim 1, wherein the reactor is at least one reactor selected from the group consisting of a microchannel reactor, a static mixer and a tubular reactor.

11. The method according to claim 1, wherein in step (4), a reaction temperature of the reaction solution C in the reactor is −30 to 80° C.

12. The method according to claim 1, wherein in step (4), a reaction time of the reaction solution C in the reactor is 0.01 to 10 min.

13. The method according to claim 1, wherein the organic solvent feed liquid A in step (1) and the mixed feed liquid B in step (2) are introduced continuously into the temperature-controllable micromixer through a material conveying equipment and mixed; and the reaction solution C is introduced continuously into the reactor and reacted to obtain the reaction solution containing citalopram diol of formula 1.

14. The method according to claim 1, wherein in step (5), the post-treating comprises:
quenching the reaction solution containing citalopram diol of formula 1, extracting, acidizing and extracting, crystallizing, centrifuging and drying to obtain the citalopram diol salt; optionally, concentrating after quenching.

15. The method according to claim 1, wherein in step (5), the post-treating comprises:
quenching the reaction solution containing citalopram diol of formula 1 using at least one of saturated ammonium chloride solution, citric acid solution or water, to obtain a quenched reaction solution;
optionally, concentrating the quenched reaction solution, to obtain a concentrated reaction solution;
adding an extraction solvent to the quenched reaction solution or the concentrated reaction solution, removing a first aqueous phase after layering and retaining a first organic phase; wherein the extraction solvent is an organic solvent insoluble with water;
adding an acid aqueous solution to the first organic phase, removing a second organic phase after layering and retaining a second aqueous phase; wherein a pH of the second aqueous phase is 3.5-4.5;
cooling the second aqueous phase for crystallization;
centrifuging and drying a precipitated crystal to obtain the citalopram diol salt.

16. The method according to claim 1, wherein the citalopram diol salt is at least one of hydrochloride, hydrobromide, sulfate or phosphate.

17. The method according to claim 3, wherein the organic solvent of the organic solvent feed liquid A is at least one of diethyl ether, tetrahydrofuran, 2-methyltetrahydrofuran or toluene.

18. The method according to claim 9, wherein the temperature-controllable passive micromixer is a stratified flow micromixer or a chaotic advection micromixer; and the temperature-controllable active micromixer is selected from the group consisting of an ultrasonically actuated micromixer, an acoustic bubbling micromixer, a droplet micromixer, a magnetic micromixer and an electrokinetic micromixer.

19. The method according to claim 15, wherein the extraction solvent is selected from the group consisting of ethyl acetate, toluene, diethyl ether and 2-methyltetrahydrofuran.

20. The method according to claim 15, wherein the acid is at least one acid selected from the group consisting of hydrochloric acid, hydrobromic acid, sulfuric acid and phosphoric acid.

* * * * *